(12) United States Patent
Liu et al.

(10) Patent No.: US 11,357,973 B2
(45) Date of Patent: Jun. 14, 2022

(54) NECK-HANGING MASSAGING DEVICE

(71) Applicant: GUANGDONG SKG INTELLIGENT TECHNOLOGY CO., LTD, Guangdong (CN)

(72) Inventors: Jie Liu, Guangdong (CN); Zhiguo Wang, Guangdong (CN); Hua Xiao, Guangdong (CN); Yanfei Chen, Guangdong (CN)

(73) Assignee: Guangdong SKG Intelligent Technology Co., Ltd., Guangdong (CN)

( * ) Notice: Subject to any disclaimer, the term of this patent is extended or adjusted under 35 U.S.C. 154(b) by 0 days.

(21) Appl. No.: 16/812,739

(22) Filed: Mar. 9, 2020

(65) Prior Publication Data
US 2020/0206493 A1   Jul. 2, 2020

Related U.S. Application Data

(63) Continuation of application No. PCT/CN2018/097373, filed on Jul. 27, 2018.

(30) Foreign Application Priority Data

Mar. 29, 2018 (CN) .......................... 201810275506.1
Mar. 29, 2018 (CN) .......................... 201820443370.6

(51) Int. Cl.
*A61N 1/04* (2006.01)
*A61N 1/36* (2006.01)
(Continued)

(52) U.S. Cl.
CPC .......... *A61N 1/0484* (2013.01); *A61N 1/0452* (2013.01); *A61N 1/36021* (2013.01)

(58) Field of Classification Search
CPC ...... A61N 1/0452; A61N 1/0484; A61N 1/32; A61N 1/36021; A61H 2201/02–107
(Continued)

(56) References Cited

U.S. PATENT DOCUMENTS 6,924,469 B1 * 8/2005 Strong ................. H05B 6/6435
                                                    219/506
10,061,352 B1 * 8/2018 Trail .................. G02B 27/0172
(Continued)

FOREIGN PATENT DOCUMENTS

CN      203842179 U     9/2014
CN      203852564 U    10/2014
(Continued)

OTHER PUBLICATIONS

The Extended European Search Report issued in corresponding EP Application No. EP18911746.8, dated Feb. 8, 2021, 5 pages.

*Primary Examiner* — Jonathan T Kuo
*Assistant Examiner* — Vynn V Huh
(74) *Attorney, Agent, or Firm* — IP Spring

(57) ABSTRACT

A neck-hanging massaging device includes an elastic arm, a first handle, a second handle, an electrode assembly and an electric pulse generating device. The first handle and the second handle are fixedly connected to the two sides of the elastic arm. The electrode assembly is arranged on the elastic arm. The electric pulse generating device is electrically connected with the electrode assembly. The electric pulse generating device is arranged in the first handle.

19 Claims, 6 Drawing Sheets

(51) Int. Cl.
*A61N 1/32* (2006.01)
*A61H 39/00* (2006.01)

(58) Field of Classification Search
USPC ........................................ 607/1–95, 115–156
See application file for complete search history.

(56) References Cited

U.S. PATENT DOCUMENTS

| | | | | |
|---|---|---|---|---|
| 2005/0197599 | A1* | 9/2005 | Yu | A61H 39/002 |
| | | | | 601/21 |
| 2009/0082831 | A1* | 3/2009 | Paul | A61N 1/0472 |
| | | | | 607/59 |
| 2016/0309808 | A1* | 10/2016 | Armour | A61F 5/055 |
| 2017/0252562 | A1* | 9/2017 | Goldwasser | A61N 1/0456 |
| 2018/0296879 | A1* | 10/2018 | Blium | A63B 21/4003 |
| 2018/0318581 | A1* | 11/2018 | Ho | A61N 1/36021 |

FOREIGN PATENT DOCUMENTS

| | | |
|---|---|---|
| CN | 204106848 U | 1/2015 |
| CN | 104856856 A | 8/2015 |
| CN | 204767037 U | 11/2015 |
| CN | 106994061 A | 8/2017 |
| CN | 108653916 A | 10/2018 |

\* cited by examiner

NECK-HANGING MASSAGING DEVICE

FIELD

The present disclosure relates to a massaging device, more particularly, to a neck-hanging massaging device for massaging a neck of a user.

BACKGROUND

In recent years, due to work and bad living habits, cervical spondylosis has youth-oriented tendency. Prior neck massaging device may normally include a main body, a left handle and a right handle. The main body is internally provided with an electric pulse generating device and an electrode assembly. The left handle and the right handle are movably connected to the two sides of the main body, i.e., the left handle may swing with the joint of the left handle with the main body as a fulcrum, and the right handle may swing with the joint of the right handle with the main body as a fulcrum. A spring is arranged between the left handle and the main body, and another spring is arranged between the right handle and the main body. Clamping force of the massaging device is provided by the springs on the left side and the right side.

However, in order not to damage the electric pulse generating device, the main body of the existing massaging device is of a rigid and anti-deformation structure, the massaging device cannot be matched with the neck in dimension. Accordingly, the electrode assembly cannot attach to the skin well, and acmesthesia feeling may be caused accordingly. In addition, the skin or hair of a user is often caught by the joints between the handles and the main body, which is not convenient for use. In addition, the springs are usually high in elastic force and not liable to deform, and consequently consumers are prone to feeling uncomfortable after long-term wearing, especially at the carotid artery.

SUMMARY

The present disclosure is mainly aimed to provide a neck-hanging massaging device, which may be adaptable to human necks of different dimension.

According to an embodiment of the present disclosure, a neck-hanging massaging device may be provided, which may include an elastic arm, a first handle and a second handle fixedly connected to ends of the elastic arm respectively, an electrode assembly arranged on the elastic arm, and an electric pulse generating device electrically connected with the electrode assembly and arranged in the first handle.

According to an embodiment of the present disclosure, the elastic arm may include a first outer shell and a first inner shell; the first inner shell may be buckled with the first outer shell; the first handle includes a second outer shell and a second inner shell; the second inner shell may be buckled with the second outer shell; the second handle includes a third outer shell and a third inner shell; the third inner shell may be buckled with the third outer shell; and the first outer shell, the second outer shell and the third outer shell may be integrally molded.

According to an embodiment of the present disclosure, the first outer shell, the second outer shell and the third outer shell may be made of plastic.

According to an embodiment of the present disclosure, the first outer shell, the second outer shell and the third outer shell may be made of stainless-steel sheet.

According to an embodiment of the present disclosure, the first handle and the second handle may be connected with the elastic arm through collars.

According to an embodiment of the present disclosure, the neck-hanging massaging device may further include a battery which may be electrically connected with the electric pulse generating device and arranged in the second handle.

According to an embodiment of the present disclosure, the neck-hanging massaging device may further include a battery which may be electrically connected with the electric pulse generating device and arranged in the first handle, and a counterweight may be arranged in the second handle.

According to an embodiment of the present disclosure, the first handle may include a second outer shell and a second inner shell. The second inner shell may be buckled with the second outer shell. The second handle may include a third outer shell and a third inner shell. The third inner shell may be buckled with the third outer shell; and the second inner shell and the third inner shell may be made of plastic.

According to an embodiment of the present disclosure, the first handle further may include a first silicone rubber sleeve; the first silicone rubber sleeve may be attached to the outer surface of the second inner shell. The second handle may further include a second silicone rubber sleeve, and the second silicone rubber sleeve may be attached to the outer surface of the third inner shell.

According to an embodiment of the present disclosure, a first sponge may be attached to the inner surface of the second inner shell. And a second sponge may be attached to the inner surface of the third inner shell.

According to an embodiment of the present disclosure, the middle of the second inner shell may be recessed inwards to form a first recessed portion, first protrusion portions may be arranged at the two ends of the first recessed portion, the middle of the third inner shell may be recessed inwards to form a second recessed portion, and second protrusion portions may be arranged at the two ends of the second recessed portion.

According to an embodiment of the present disclosure, the elastic arm may include a first outer shell and a first inner shell, the first inner shell may be buckled with the first outer shell. One of the first outer shell and the first inner shell may be provided with a groove, and a protrusion may be arranged on the other of the first outer shell and the first inner shell; and the protrusion may be arranged in the groove.

According to an embodiment of the present disclosure, the first outer shell and the first inner shell may be also bonded through an adhesive.

According to an embodiment of the present disclosure, the elastic arm may include a first outer shell and a first inner shell, the first inner shell may be buckled with the first outer shell, and the first inner shell may be made of silicone rubber.

According to an embodiment of the present disclosure, the elastic arm may include a first outer shell and a first inner shell, the first inner shell may be buckled with the first outer shell; and the space between the first outer shell and the first inner shell may be filled with a third sponge.

According to an embodiment of the present disclosure, the electrode assembly may be in a long-strip shape and may be arranged in the extending direction of the elastic arm.

According to an embodiment of the present disclosure, the neck-hanging massaging device further includes a remote control device which may be magnetically attached to the first handle or the second handle.

According to the neck-hanging massaging device of the present disclosure, by arranging the electric pulse generating device and the battery on the first handle and the second handle, and connecting the first handle and the second handle through the elastic arm, the neck-hanging massaging device may be worn through deformation of the elastic arm, and the neck-hanging massaging device may well adapted to the size or dimension of the neck without damaging the electric pulse generating device. In addition, Due to gravity of the first handle, the second handle, the electric pulse generating device and the battery, the electrode assembly may be comfortably attached to the neck without causing acmesthesia feeling. Moreover, the skin or hair of users may not be caught at the joint between the left handle or the right handle and the main body. Besides, the deformation of the elastic arm may depend on the form change of itself, rather than the high non-deformable elastic force of the springs, so the elastic force of the neck-hanging massaging device of the present disclosure may make the user feel softer and more comfortable.

BRIEF DESCRIPTION OF THE DRAWINGS

In order to explain the technical solutions in the embodiments of the present disclosure or the prior art more clearly, the drawings used by the description of the embodiments or the prior art will be briefly introduced below. Obviously, the drawings in the following description may be merely some embodiments of the present disclosure. For those of ordinary skilled in the art, other drawings may be obtained according to the structures shown in the drawings without creative effort, in which.

DETAILED DESCRIPTION

In the following, the technical solutions in the embodiments of the present disclosure will be clearly and completely described with reference to the drawings in the embodiments of the present disclosure. Obviously, the described embodiments may be only a part of the embodiments of the present disclosure, but not all of the embodiments. Based on the embodiments of the present disclosure, all other embodiments obtained by those of ordinary skilled in the art without creative effort shall fall within the protection scope of the present disclosure.

In addition, descriptions such as "first" and "second" in the present disclosure may be for descriptive purposes only, and cannot be understood as indicating or implying the relative importance or implicitly indicating the number of indicated technical features. Therefore, the features defined as "first" and "second" may explicitly or implicitly include at least one of the features. In the description of the present disclosure, the meaning of "a plurality of" may be at least two, for example, two, three and so on, unless it may be specifically defined otherwise.

According to the present disclosure, the terms "connection", "fixing" and the like should be understood in a broad sense unless otherwise specified and defined, for example, "fixing" may be fixed connection or detachable connection or an integral whole, may be mechanical connection or electrical connection, may be direct connection or indirect connection through an intermediate medium, and may be internal connection of two elements or interaction between two elements, unless it may be clearly defined otherwise. For those of ordinary skilled in the art, the specific meanings of the above terms in the present disclosure may be understood according to specific situations.

In addition, the technical solutions between the various embodiments of the present disclosure may be combined with each other, but must be based on what may be achieved by those of ordinary skilled in the art. When the combination of technical solutions conflicts or cannot be achieved, such a combination of technical solutions should be considered to be nonexistent and not within the scope of protection claimed by the present disclosure.

A neck-hanging massaging device 10 according to embodiments of the present disclosure will be described with reference to FIGS. 1 to 7 in the following.

Figure 1:
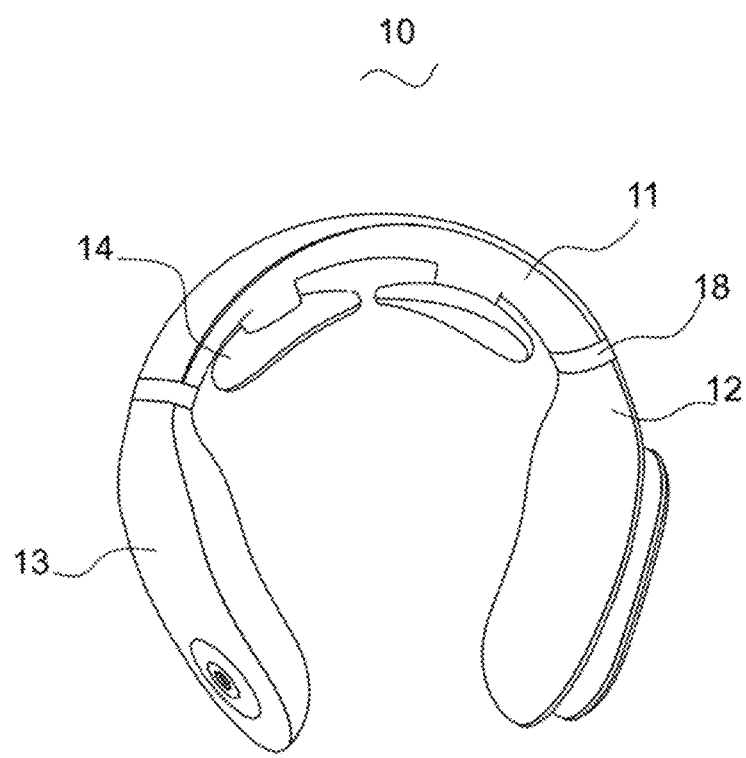
FIG. 1 is a view perspective view of a neck-hanging massaging device according to some embodiments of the present disclosure.
Figure 2:
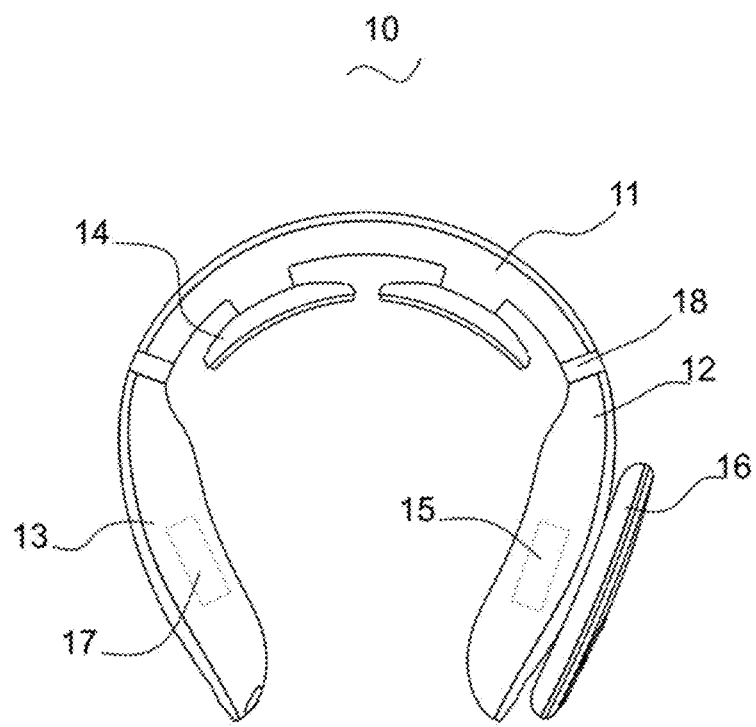
FIG. 2 is a front view of the neck-hanging massaging device shown in FIG. 1.

Referring to FIGS. 1 and 2, the neck-hanging massaging device 10 may include an elastic arm 11, a first handle 12, a second handle 13, an electrode assembly 14 and an electric pulse generating device 15. The first handle 12 and the second handle 13 may be fixedly connected to the ends of the elastic arm 11 respectively. The electrode assembly 14 may be arranged on the elastic arm 11. The electric pulse generating device 15 may be electrically connected with the electrode assembly 14. The electric pulse generating device 15 may be arranged in the first handle 12.

In order to facilitate operation, according to some embodiments of the present disclosure, as shown in FIGS. 1 and 2, the neck-hanging massaging device 10 may further include a remote control device 16. The remote control device 16 may be magnetically attached to the first handle or the second handle, and thus the remote control device 16 may be prevented from being lost.

Figure 3:
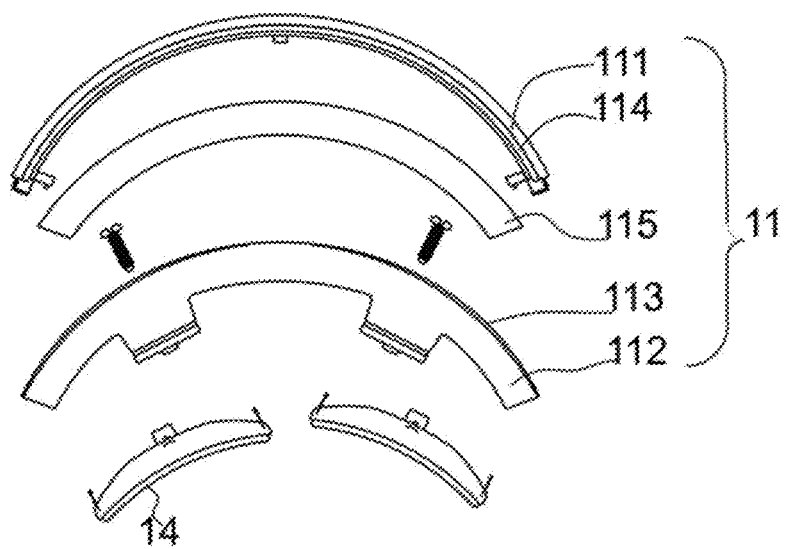
FIG. 3 is an exploded view of an elastic arm and electrode assembly shown in FIG. 1.

As shown in FIG. 3, the elastic arm 11 may include a first outer shell 111 and a first inner shell 112. The first inner shell 112 may be buckled with the first outer shell 111. Specifically, a groove 113 may be formed in one of the first outer shell 111 and the first inner shell 112, the other of the first outer shell 111 and the first inner shell 112 may be provided with a protrusion 114, and the protrusion 114 may be arranged in the groove 113, so that the first outer shell 111 and the first inner shell 112 may be connected conveniently. In some embodiments, in order to assemble the first outer shell 111 and the first inner shell 112 more stably, the first outer shell 111 and the first inner shell 112 may be further bonded through an adhesive.

In some embodiments, the first inner shell 112 may be made of silicone rubber so as to be attached to the skin conveniently and make people feel comfortable. In addition, compared with plastic materials in the art, friction force between the elastic arm 11 and the human neck skin may be increased through contact of the silicone rubber and the skin, thus, the massaging device 10 may twist along with twist of the human neck. Thus, the massaging device 10 according to the embodiments of the present disclosure may be attached to the human neck more comfortably and stably, and the acmesthesia feeling caused by the electrode assembly 14 occasionally when detaching from the skin of a user may be avoided accordingly.

In addition, as shown in FIG. 3, the space between the first outer shell 111 and the first inner shell 112 may be filled with a third sponge 115. In this way, the elastic arm 11 may be fuller, and the skin comfortableness may be further increased.

Figure 5:
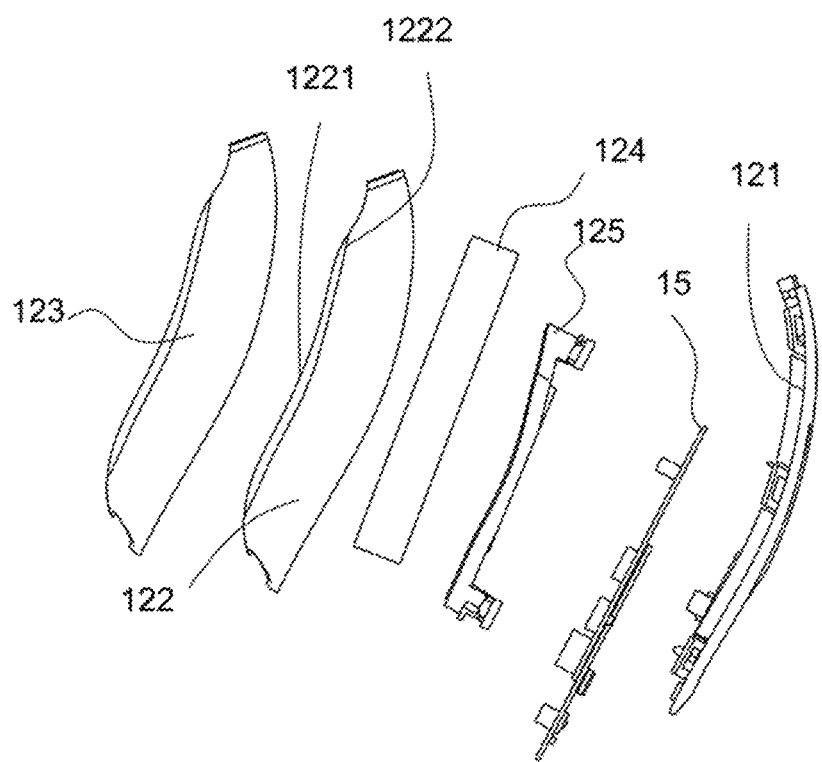
FIG. 5 is an exploded view of a second handle shown in FIG. 1.

As shown in FIG. 5, the first handle 12 may include a second outer shell 121 and a second inner shell 122, and the second inner shell 122 may be buckled with the second outer shell 121. In some embodiments, the second outer shell 121 and the second inner shell 122 may be both made of plastic. Therefore, the electric pulse generating device 15 in the first handle 12 may be better protected, and when the neck-hanging massaging device 10 may be used, the electric pulse generating device 15 being damaged due to deformation of the first handle 12 may be avoided.

Figure 4:
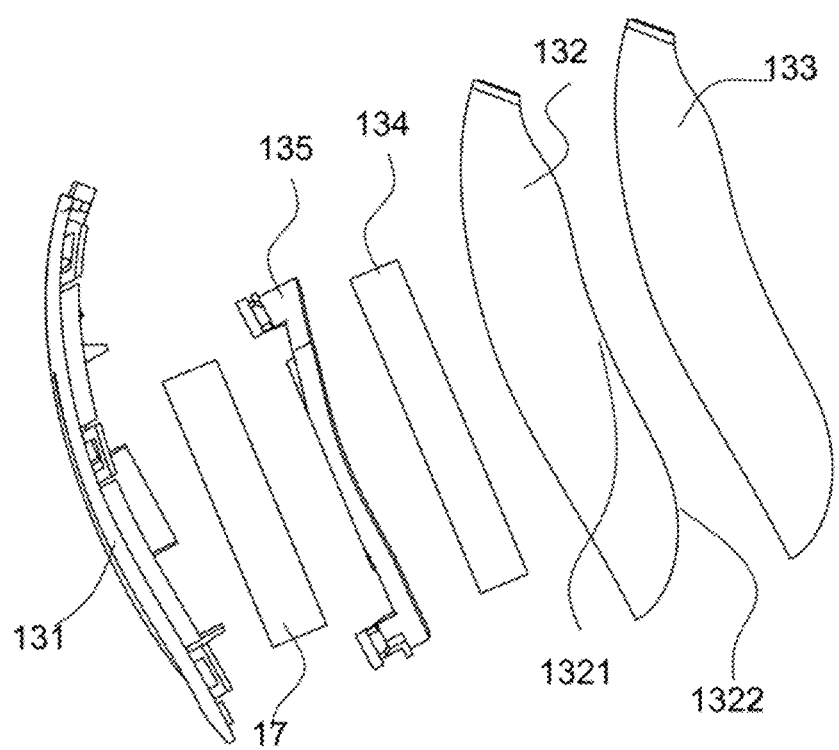
FIG. 4 is an exploded view of a first handle shown in FIG. 1.

As shown in FIG. 4, the second handle 13 may include a third outer shell 131 and a third inner shell 132. The third inner shell 132 may be buckled with the third outer shell 131. A battery 17 may be mounted in the second handle 13. In some embodiments, the third outer shell 131 and the third inner shell 132 may be both made of plastic. Therefore, the battery 17 in the second handle 13 may be better protected, and the situation that when the neck-hanging massaging device 10 may be used, the battery 17 may be damaged due to deformation of the second handle 13 may be avoided. The electric pulse generating device 15 and the battery 17 may be mounted in the first handle 12 and the second handle 13 respectively, so that the weight of the neck-hanging massaging device 10 may be balanced, and stable wearing may be facilitated.

According to some optional examples of the present disclosure, in order to increase the comfort, the first handle 12 may further include a first silicone rubber sleeve 123, as shown in FIG. 5. The shape of the first silicone rubber sleeve 123 may be substantially the same as that of the second inner shell 122. The first silicone rubber sleeve 123 may be attached to the outer surface of the second inner shell 122. Similarly, the second handle 13 may include a second silicone rubber sleeve 133, as shown in FIG. 4. The second silicone rubber sleeve 133 may be attached to the outer surface of the third inner shell 133.

Further, referring to FIG. 5, a first sponge 124 may be attached to the inner surface of the second inner shell 122. The first sponge 124 may be located between the second inner shell 122 and the electric pulse generating device 15. In this way, the electrical pulse generating device 15 may be buffered and protected, and the hand feeling during attaching to the electrical pulse generating device 15 may be improved. Similarly, a second sponge 134 may be attached to the inner surface of the third inner shell 133, as shown in FIG. 4.

When the neck-hanging massaging device 10 may be used, the second handle 13 and the third handle 14 jointly grip the human neck. In some embodiments, in order to prevent the second handle 13 and the third handle 14 from squeezing the carotid artery of the neck, as shown in FIG. 5, the middle of the second inner shell 122 may be recessed inwards to form a first recessed portion 1221. First protrusion portions 1222 may be arranged at the two ends of the first recessed portion 1221, as shown in FIG. 5. The first recessed portion 1221 may be used to keep away from the carotid artery. Similarly, as shown in FIG. 4, the middle of the third inner shell 132 may be recessed inwards to form a second recessed portion 1321. Second protrusion portions 1322 may be arranged at the two ends of the second recessed portion 1321, as shown in FIG. 4.

According to some embodiments of the present disclosure, the first handle 12, the second handle 13 and the elastic arm 11 may be designed in a split mode. Specifically, as shown in FIG. 1 and FIG. 2, the first handle 12 may be connected with the elastic arm 11 through a collar 18. The second handle 13 may be connected with the elastic arm 11 through a collar 18. The collars 18 may prevent the first handle 12 and the second handle 13 from being deformed along with the elastic arm 11, and therefore electrical elements in the first handle 12 and the second handle 13 may be protected accordingly. To further increase the rigidity of the first handle 12 and the second handle 13, electrical elements, such as the electric pulse generating device 15 and the battery 17 etc, may be mounted through a rigid supporting members 125, 135 respectively.

In some embodiments, as shown in FIGS. 1-3 and FIGS. 6-7, the electrode assembly 14 may be of a long-strip shape. The electrode assembly 14 may be arranged in the extending direction of the elastic arm 11 as shown in FIGS. 1-3 and FIGS. 6-7, so that the electrode assembly 14 may be better attached to the human neck, and the acmesthesia feeling caused by the electrode assembly 14 occasionally when detaching from the skin may be avoided.

When the neck-hanging massaging device 10 may be assembled, the electric pulse generating device 15 may be mounted in the first handle 12 at first, and the battery 17 may be mounted in the second handle 13. Then, the second outer shell 121 and the second inner shell 122 may be buckled together, and the third outer shell 131 and the third inner shell 132 may be buckled together. Then, the first outer shell 111 and the first inner shell 112 may be buckled together. Finally, the first handle 12 may be connected with the elastic arm 11 through the collar 18, and the second handle 13 may be connected to the elastic arm 11 through the other collar 18.

When the neck-hanging massaging device 10 may be used, a user may hold the first handle 12 and the second handle 13 and separate the first handle 12 and the second handle 13 to a certain angle, so that the elastic arm 11 may be elastically deformed. Then, the neck-hanging massaging device 10 may be put on the neck, and the electrode assembly on the elastic arm 11 may be attached to the neck. Finally, the user may slowly release the first handle 12 and the second handle 13. At this time, depending on the resilient force of the elastic arm 11, the first handle 12 and the second handle 13 may clamp the neck. Since the resilient shape of the elastic arm 11 may adapt to the size of the necks of different users, the electrode assembly 14 may be well attached to the skin, and the acmesthesia feeling may be avoided. It should be pointed out that when the size of the neck of the user may be small, the elastic arm 11 may be completely restored without generating elastic force, and the first handle 12 and the second handle 13 may not clamp the neck accordingly.

Further, by arranging the electric pulse generating device 15 on the first handle 12 and the battery 17 on the second handle 13, the size of the elastic arm 11 may be prevented from being too large, and the weight of the whole neck-hanging massaging device 10 may be balanced. Under the gravity of the first handle 12, the second handle 13, the electric pulse generating device 15 and the battery 17, the electrode assembly 14 may be comfortably attached to the neck.

According to the neck-hanging massaging device 10 according to the embodiments of the present disclosure, the electric pulse generating device 15 and the battery 17 may be arranged in the first handle 12 and the second handle 13, the elastic arm 11 may connect the first handle 12 with the second handle 13, a user may wear the neck-hanging massaging device 10 through deformation of the elastic arm 11, and the massaging device may well adapt to the size of the neck without damaging the electric pulse generating device 15. In addition, under the gravity of the first handle 12, the second handle 13, the electric pulse generating device 15 and the battery 17, the electrode assembly 14 may be comfortably attached to the neck without causing acmesthesia feeling. Moreover, the skin or hair of the user will not be caught at the joint between the left handle or the right handle and the main body. In addition, deformation of the elastic arm 11 may depend on the form change of the elastic arm 11 itself, rather than the high non-deformable elastic force of the springs. Therefore, the elastic force of the neck-hanging massaging device 10 may make the user feel softer and more comfortable.

Figure 6:
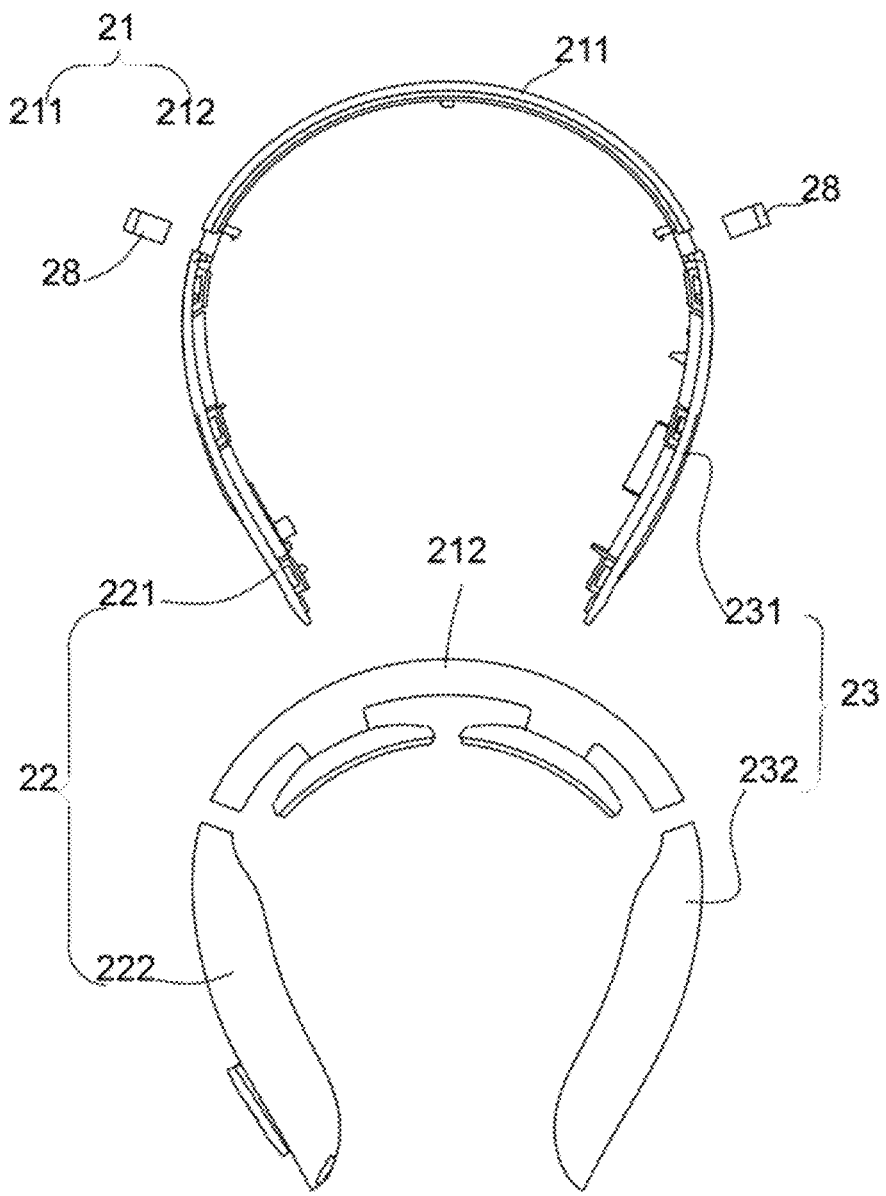
FIG. 6 is a schematic view of a neck-hanging massaging device according to another embodiments of the present disclosure.

According to other embodiments of the present disclosure, as shown in FIG. 6, the elastic arm 21 may include a first outer shell 211 and a first inner shell 212, and the first inner shell 212 may be buckled with the first outer shell 211. The first handle 22 may include a second outer shell 221 and a second inner shell 222, and the second inner shell 222 may be buckled with the second outer shell 221. The second handle 23 may include a third outer shell 231 and a third inner shell 232. The third inner shell 232 may be buckled with the third outer shell 231. The first outer shell 211, the second outer shell 221 and the third outer shell 231 may be integrally molded.

In some embodiments, the first outer shell 211, the second outer shell 221 and the third outer shell 231 may be made of elastically deformable materials, such as plastic. However, since the overall structure formed by connecting the first outer shell 211, the second outer shell 221 and the third outer shell 231 may be approximately in a C shape, elastic deformation may be achieved to a certain extent, and in particular, the first outer shell 211 may have a higher elastic deformation degree.

In the embodiment, although the first outer shell 211, the second outer shell 221 and the third outer shell 231 may be integrally molded, collars 28 may still be arranged between the first handle 12 and the elastic arm 11 as well as between the second handle 13 and the elastic arm 11. According to an embodiment of the present disclosure, the first handle 12 and the second handle 13 may be prevented from being deformed with the elastic arm 11 through the collars, and therefore electrical elements in the first handle 12 and the second handle 13 may be protected.

The present disclosure may be not limited to the embodiments described herein, and the first outer shell 211, the second outer shell 221 and the third outer shell 231 may also be stainless steel sheets or the like.

Figure 7:
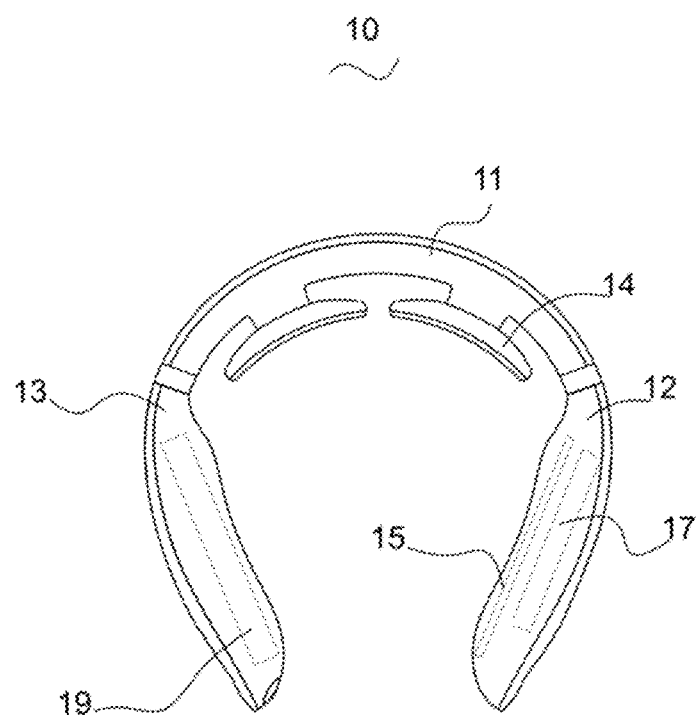
FIG. 7 is a partial exploded view of a neck-hanging massaging device according to still another embodiments of the present disclosure.

According to further embodiments of the present disclosure, as shown in FIG. 7, in the neck-hanging massaging device 10, both the electric pulse generating device 15 and the battery 17 may be arranged in the first handle 12, and a counterweight 19 may be arranged in the second handle 13. The weight of the counterweight 19 may be substantially equal to the sum of the weights of the electric pulse generating device 15 and the battery 17. Therefore, the weight balance of the neck-hanging massaging device 10 may be ensured accordingly.

The above descriptions may be only preferred embodiments of the present disclosure, and thus do not limit the patent claims of the present disclosure. Any equivalent structural transformation made by using the description and drawings of the present disclosure under the concept of the present disclosure, or direct/indirect application in other related technical fields may be included in the patent protection scope of the present disclosure.

The invention claimed is:

1. A neck-hanging massaging device, comprising:
   an elastic arm;
   a first handle fixedly connected to one end of the elastic arm;
   a second handle fixedly connected to the other end of the elastic arm;
   an electrode assembly arranged on the elastic arm;
   an electric pulse generating device electrically connected with the electrode assembly, which is arranged in the first handle to increase a weight of the first handle; and
   a battery powering the electric pulse generating device, wherein the battery is arranged in one of the first handle and the second handle to increase the weight of the corresponding handle, in such a manner that under the gravity of the first handle, the second handle, the electric pulse generating device and the battery, the electrode assembly is configured to be attached to the neck when the neck-hanging massaging device is worn, wherein the first handle and the second handle are connected with the elastic arm through collars respectively, and wherein the collars are configured to prevent the first handle and the second handle from being deformed along with the elastic arm, and configured to protect electrical elements in the first handle and the second handle.

2. The neck-hanging massaging device according to claim 1, wherein
   the elastic arm comprises a first outer shell and a first inner shell which is buckled with the first outer shell;
   the first handle comprises a second outer shell and a second inner shell which is buckled with the second outer shell;
   the second handle comprises a third outer shell and a third inner shell which is buckled with the third outer shell; and
   the first outer shell, the second outer shell and the third outer shell are integrally molded.

3. The neck-hanging massaging device according to claim 2, wherein the first outer shell, the second outer shell and the third outer shell are made of plastic.

4. The neck-hanging massaging device according to claim 2, wherein the first outer shell, the second outer shell and the third outer shell are made of stainless-steel sheet.

5. The neck-hanging massaging device according to claim 1, wherein the battery is arranged in the second handle.

6. The neck-hanging massaging device according to claim 1, wherein the battery is arranged in the first handle, and a counterweight is arranged in the second handle.

7. The neck-hanging massaging device according to claim 1, wherein the first handle comprises a second outer shell and a second inner shell, and the second inner shell is buckled with the second outer shell;
   the second handle comprises a third outer shell and a third inner shell, and the third inner shell is buckled with the third outer shell; and the second inner shell and the third inner shell are made of plastic.

8. The neck-hanging massaging device according to claim 7, wherein the first handle further comprises a first silicone rubber sleeve attached to an outer surface of the second inner shell; and
the second handle further comprises a second silicone rubber sleeve attached to an outer surface of the third inner shell.

9. The neck-hanging massaging device according to claim 8, wherein a first sponge is attached to an inner surface of the second inner shell, and a second sponge is attached to an inner surface of the third inner shell.

10. The neck-hanging massaging device according to claim 7, wherein the middle of the second inner shell is recessed inwards to form a first recessed portion, and first protrusion portions are arranged at the two ends of the first recessed portion; and
the middle of the third inner shell is recessed inwards to form a second recessed portion, and second protrusion portions are arranged at the two ends of the second recessed portion.

11. The neck-hanging massaging device according to claim 1, wherein the elastic arm comprises a first outer shell and a first inner shell, the first inner shell is buckled with the first outer shell, a groove is formed in one of the first outer shell and the first inner shell, a protrusion is arranged on the other of the first outer shell and the first inner shell, and the protrusion is arranged in the groove.

12. The neck-hanging massaging device according to claim 11, wherein the first outer shell and the first inner shell are further bonded through an adhesive.

13. The neck-hanging massaging device according to claim 1, wherein the elastic arm comprises a first outer shell and a first inner shell, the first inner shell is buckled with the first outer shell, and the first inner shell is made of silicone rubber.

14. The neck-hanging massaging device according to claim 1, wherein the elastic arm comprises a first outer shell and a first inner shell, the first inner shell is buckled with the first outer shell, and space between the first outer shell and the first inner shell is filled with a third sponge.

15. The neck-hanging massaging device according to claim 1, wherein the electrode assembly is of a long-strip shape, which is arranged in an extending direction of the elastic arm.

16. The neck-hanging massaging device according to claim 1, further comprising a remote control device magnetically attachable to the first handle or the second handle.

17. A neck-hanging massaging device, comprising:
an elastic arm;
a first handle fixedly connected to one end of the elastic arm;
a second handle fixedly connected to the other end of the elastic arm;
an electrode assembly arranged on the elastic arm;
an electric pulse generating device electrically connected with the electrode assembly, which is arranged in the first handle to increase a weight of the first handle; and
a battery powering the electric pulse generating device, wherein the battery is arranged in one of the first handle and the second handle to increase the weight of the corresponding handle, in such a manner that under the gravity of the first handle, the second handle, the electric pulse generating device and the battery, the electrode assembly is configured to be attached to the neck when the neck-hanging massaging device is worn, wherein:
the elastic arm comprises a first outer shell configured to be placed away from the neck and a first inner shell configured to face towards the neck,
the first inner shell is buckled with the first outer shell,
to buckle the first inner shell with the first outer shell, a groove is formed in one of the first outer shell and the first inner shell, and the other of the first outer shell and the first inner shell is provided with a protrusion, and the protrusion is arranged in the groove,
the electrode assembly is arranged on the first inner shell of the elastic arm, and
the first inner shell is made of silicone rubber configured to make the electrode assembly movable, and the first outer shell is made of plastic or stainless-steel sheet, and
wherein:
the first handle comprises a second outer shell and a second inner shell which is buckled with the second outer shell,
the second handle comprises a third outer shell and a third inner shell which is buckled with the third outer shell, and
the first outer shell, the second outer shell, and the third outer shell are integrally molded.

18. The neck-hanging massaging device according to claim 17, wherein the first outer shell, the second outer shell and the third outer shell are made of plastic or stainless-steel sheet.

19. A neck-hanging massaging device, comprising:
an elastic arm;
a first handle fixedly connected to one end of the elastic arm;
a second handle fixedly connected to the other end of the elastic arm;
an electrode assembly arranged on the elastic arm;
an electric pulse generating device electrically connected with the electrode assembly, which is arranged in the first handle to increase a weight of the first handle; and
a battery powering the electric pulse generating device, wherein the battery is arranged in one of the first handle and the second handle to increase the weight of the corresponding handle, in such a manner that under the gravity of the first handle, the second handle, the electric pulse generating device and the battery, the electrode assembly is configured to be attached to the neck when the neck-hanging massaging device is worn, wherein:
the elastic arm comprises a first outer shell configured to be placed away from the neck and a first inner shell configured to face towards the neck,
the first inner shell is buckled with the first outer shell,
to buckle the first inner shell with the first outer shell, a groove is formed in one of the first outer shell and the first inner shell, and the other of the first outer shell and the first inner shell is provided with a protrusion, and the protrusion is arranged in the groove,
the electrode assembly is arranged on the first inner shell of the elastic arm,
the first inner shell is made of silicone rubber configured to increase friction force between the elastic arm and skin of the neck, and
the first outer shell is made of plastic or stainless-steel sheet, and
wherein:

the first handle comprises a second outer shell and a second inner shell which is buckled with the second outer shell, the second handle comprises a third outer shell and a third inner shell which is buckled with the third outer shell, and the first outer shell, the second outer shell, and the third outer shell are integrally molded.

\* \* \* \* \*